(12) United States Patent
Postrel

(10) Patent No.: US 11,468,973 B2
(45) Date of Patent: Oct. 11, 2022

(54) LEVERAGING GENOMIC, PHENOTYPIC AND PHARMACOLOGICAL DATA TO CURE DISEASE

(71) Applicant: Richard Postrel, Miami Beach, FL (US)

(72) Inventor: Richard Postrel, Miami Beach, FL (US)

(*) Notice: Subject to any disclaimer, the term of this patent is extended or adjusted under 35 U.S.C. 154(b) by 1214 days.

(21) Appl. No.: 15/954,575

(22) Filed: Apr. 16, 2018

(65) Prior Publication Data

US 2019/0243945 A1 Aug. 8, 2019

Related U.S. Application Data

(60) Provisional application No. 62/625,962, filed on Feb. 2, 2018.

(51) Int. Cl.
| | | |
|---|---|---|
| *G01N 33/48* | (2006.01) | |
| *G01N 33/50* | (2006.01) | |
| *G16C 20/40* | (2019.01) | |
| *G16C 20/50* | (2019.01) | |
| *C40B 30/00* | (2006.01) | |
| *G16C 20/70* | (2019.01) | |
| *G16B 5/00* | (2019.01) | |
| *G16C 20/90* | (2019.01) | |
| G16B 20/00 | (2019.01) | |
| A61K 31/352 | (2006.01) | |
| A61K 31/52 | (2006.01) | |
| G01N 33/94 | (2006.01) | |

(52) U.S. Cl.
CPC .............. *G16C 20/40* (2019.02); *C40B 30/00* (2013.01); *G01N 33/5008* (2013.01); *G16B 5/00* (2019.02); *G16C 20/50* (2019.02); *G16C 20/70* (2019.02); *G16C 20/90* (2019.02); *A61K 31/352* (2013.01); *A61K 31/52* (2013.01); *G01N 33/94* (2013.01); *G01N 2500/00* (2013.01); *G16B 20/00* (2019.02)

(58) Field of Classification Search
CPC ........ G16C 20/40; G16C 20/50; G16C 20/90; G16C 20/70; C40B 30/00; G16B 5/00; G16B 20/00; A61K 31/05; A61K 31/352; A61K 31/52; G01N 33/94; G01N 2500/00

See application file for complete search history.

(56) References Cited

U.S. PATENT DOCUMENTS

| | | | | |
|---|---|---|---|---|
| 2001/0041964 A1* | 11/2001 | Grass | ..................... | G16C 20/62 422/68.1 |
| 2002/0098493 A1* | 7/2002 | Nathan | ................... | C40B 40/02 536/23.1 |
| 2004/0117125 A1* | 6/2004 | Chen | ..................... | G16C 20/64 702/22 |

* cited by examiner

*Primary Examiner* — Russell S Negin

(57) ABSTRACT

The present invention provides a process and method for repurposing existing compounds by leveraging genomic, phenotypic and pharmacological data to cure disease. Applying advanced mathematical analytics using massively interconnected computing capabilities to identify target rich sets of existing compounds available for animal testing at the earliest stage in the process collapses cycle time of development, dramatically reducing costs. Target rich sets obtained through this invention produce compounds or compositions which each have a demonstrated ability to modulate disease or an associated phenotypic expression. By rendering the mechanism of action irrelevant, this invention collapses the time and cost to discovery of an efficacious drug from decades to days and from $Billions to $Millions.

11 Claims, No Drawings

LEVERAGING GENOMIC, PHENOTYPIC AND PHARMACOLOGICAL DATA TO CURE DISEASE

From prehistoric times mankind has recognized certain eating behaviors were essential or beneficial to health. Societies began to pass along healthy advice to their families, clans, bands, tribes and nations to form a historical record. In the most recent millennium many writings describe disease and man's responses. Modern science and published research and other reports provide a vast repository of information relating to the gamut of human interests, including many plants, compounds, foods, practices and activities related to both poor and good health. The present invention recognizes this collected human treasure and uses it as the foundational heart of a changed methodology for rapidly developing and identifying new treatments to cure disease.

Since the advent of computers and especially the internet new techniques in computing and higher mathematics can now be combined to interrogate extremely large data sets in parallel. Embodiments of the present invention through enlightened application of self-referencing libraries, fuzzy logic and artificial intelligence collapse typical cycle times and costs to discovery of new pharmaceuticals from decades to days and from billions of dollars to millions. This invention teaches that use of dry research (supercomputing) as an antecedent to wet research (traditional biological laboratories) allows multi domains to collaborate and inform one another and thereby expedite and facilitate drug discovery.

As a simplified description of this invention, a disease or symptom related to disease is recognized and selected for analysis. An algorithm searches a database or group of databases to build a library of related symptoms and diseases. For example, all diseases sharing a symptom can be categorized. Symptoms associated with these diseases are examined. Rather than looking at the phenotypic manifestations of disease processes, the algorithm derives from the database search underlying causes of the groups of symptoms and diseases. Diverse records are included. For example, some records may describe proposed cures that unsuccessfully treated a symptom; some records may describe demographic or epidemiologic factors relating to a symptom or disease; some records may correlate a complete genome, an expression library, mutation data or the like; some records may track changes in diet due to climate conditions; etc. Using these data the algorithm can select a gene or likely class or list of genes as associated with the group of symptoms and/or diseases. Knockout and/or transgenic mice are bred to support a testing program using the select library of compounds the algorithm determines from the search of database(s) to have an observed effect on or to have an observed association with the gene(s)' pathway(s). The testing program jumpstarts development by identifying compounds at least tangentially or abstractly associated with the original disease and testing only these select compounds in the mouse models. One outcome of this method may be that one or several compounds are identified for the primary disease, but that as part of this process, treatments for related diseases or at least partial treatments for diseases sharing its symptoms will be made available. Rather than starting the laboratory discovery process at the symptom level and backtracking through the relevant protein pathways and/or gene, this process aims to treat an underlying cause of disease by starting with compounds already shown to be related to the symptom or disease irrespective of knowledge of the molecular interactions underlying the effect. Cloud computing, artificial intelligence applied to stored knowledge to identify high probability targets related to the disease or diseases for repurposing using targeted confirmation by the laboratory to compress traditional early stages and collapsing cycle time to discovery of efficacious repurposed or marginally modified, e.g., congener, drugs.

The present invention elaborates an enlightened systematic approach for discovering and delivering medicaments and/or therapeutic supplement formulations. Unlike the conventional approach which is founded on a recognized symptom, followed by the symptom being associated with one or more organs or biologic systems whose component parts are assessed for likeliness of relation to the symptom(s), this new approach makes use of the massive data libraries to associate related symptoms and diseases and past chemical intervention attempts. In accordance with convention, research projects focus narrowly on a specific molecule, generally a protein involved in activating or turning off a pathway. One-by-one target pathways/proteins are selected and tested in vitro, possibly crystallizing the protein molecule bound and/or unbound to a natural or potential pharmaceutical ligand. Several generations of chemical library screenings may or may not be successful in identifying an active candidate drug. Cross reactions, e.g., with hepatic enzymes or with immune cells must be screened out. When a development program passes these hurdles, in vivo screens, including cell culture and/or primary cell assays, followed by trials using transgenic and/or knockout animal models are designed and tested for relation to the symptomatic disease. Eventually, therapeutic compounds or compositions are suggested and tested for possible efficacy usually first in human cell culture and one or more relevant animal models. Once safety and efficacy screens are satisfactorily completed, government approval is sought for larger scale human trials. Following this step-by-step process, phase 2 and phase 3 human trials may be initiated. This conventional approach is lengthy, costly and often unsuccessful in supplying a successful outcome.

In contrast, the present invention, though also recognizing symptoms, applies a vastly different approach. One or more symptom(s) associated with a particular disease is/are noted. In this context the term "symptom" relates to any observable feature associated with a disease, malady, undesired health characteristic, etc. Physical, chemical, behavioral traits, etc. may comprise symptoms, for example, twitch, compulsive behavior, insomnia, mRNA, nRNA, a mutation, hyperthermia, pain, growth, lesion, etc. But, instead of narrowing the focus to a specific pathway and its dominant protein(s), tremendous power in the relation of genomic data available for the human species, but also for all life forms is used to broaden the endeavor. Nuclear genomic information, organelle (mitochondria/chloroplasts) genomic information, bacterial genomic information, episomal genomic information, viral genomic information, expression profiles corresponding to the genetic information serves as one bridge to phenotypic expression manifest in the original disease of interest with noted associations serving to widen the discovery process by introducing into the analysis: diseases, condition, and/or symptoms sharing a trait with the original symptom/disease of interest (SDI). Using these associations, existing compounds can be brought to the forefront for testing and possible repurposing to address unmet treatment needs.

Conceptually the discovery process starts with an observable deficit or defect. A vast collection of data loosely organized in public and/or private databases is examined as a system for commonplace and for abstract—unrecognized—associations between, e.g., biologic data, symptoms, related protein targets, genetic information, diseases symptoms, families of or individual modulating compounds, pathway relations, etc.

A system preferred for use in the present invention comprises multiple files storing data in one or several structured formats, e.g., organized into tables, lists, labels, catalogues, spreadsheets, fields and the like. A single database may comprise multiple organization structures which may include reference links to other databases. The organization itself preferably should not significantly constrain achieving results from a data query.

Individual entries within a database may be independent or may cross reference to records within other databases comprising a system. A record may consist of text. However, especially when artificially intelligent processes are applied, records may be machine derived, for example, a Doppler or standard ultrasonic record which may comprise digitized expression of sound and or images with vectoring, time stamp and/or other mathematic or descriptic associations. Three spatial dimensions as well as numerous non-spatial annotations may be stored which can be projected to form one or more discoverable patterns in relevant dimensions to be determined in responding to the query. Data may be formatted or reformatted into a single comprehensive record or into multiple parallel sets for efficient query of parts or the entirety of the database system. Resource description framework organization is often compiled into files having the ".rdf" extension. But other formats for storing accessible data records or a system comprising records of different formats or even one or more record entry stored in a plurality of formats can apply in practicing the present invention. Simple space, comma or other formats used to distinguish individual values in a dataset.

Format may be open or closed. Open formats are generally preferred due to the greater number of users policing for bugs, glitches, errors, etc. A moderator will generally oversee modifications. The moderator may be or may be guided by machine learning algorithm(s). Formats may also be partially open such as identifiable data files available to certain stakeholders as allowed or restricted by federal laws and/or other regulations or conventions (for example: Centers for Medicare and Medicaid Service policy). All relevant policies, regulations, laws and common courtesies should be followed when the invention is practiced.

The National Institutes of Health and similar agencies of other governments (e.g., European Bioinformatics Institute US National Center for Biotechnology Information Swiss Institute of Bioinformatics Japanese Institute of Genetics Broad Institute Wellcome Trust Sanger Institute maintain and provide access to education, community, scientific, medical resources, etc. The US food and Drug Administration and analogous regulatory and advisory bodies collate, organize and allow public access to health and pharmaceutical information to different degrees, generally relaxing restrictions as the data age. The present invention may use, however does not require, cutting edge or proprietary data. The invention makes use of relevant selections from the tremendous volume of tabulated and more abstract data to track relationships between diseases, symptoms treatments, etc., to progress to the next stage of cell and/or animal testing.

Popular sources throughout the world including, but not limited to: Nucleic Acid Research Molecular Biology Database Collection—over 1,500 databases, World Health Organization (e.g., Traditional Aboriginal Medicine Practice In The Northern Territory, The International Pharmacopeia), *Charaka Samhita and/or Sushruta Samhita (Sushruta's Compendium)*, *Rerum Medicarum Novae Hispaniae Thesaurus,* Ayurveda treatises, Wikipedia, *Astragalus,* National Center for Complementary and Integrative Health, Smithsonian Institution, *African Traditional Medicine Pharmacopia, Cherokee pharmacopoeia medicinal plants and herbal remedies, Nature's Pharmacopeia: A World of Medicinal Plants, Canon of Medicine, General Medicine Vols.* 1-5, The Human Genome Project, NRSP-8 Bioinformatics Coordination Program, Human Genome Resources at NCBI, EMBL (European Bioinformatics Institute), The Genesis Project, National Library of Medicine, International Nucleotide Sequence Database, GenBank (National Center for Biotechnology Information), Bioinformatic Harvester, Gene Disease Database, SNPedia, Ensembl (provides automatic annotation databases for human, mouse, other vertebrate and eukaryote genomes. Ensembl Genomes provides genome-scale data for bacteria, protists, fungi, plants and invertebrate metazoa, through a unified set of interactive and programmatic interfaces (using the Ensembl software platform), Flybase, *Saccharomyces* Genome Database, Xenbase, WormBase ParaSite, Rfam, miRBase, Protein Information Resource (Georgetown University Medical Center (GUMC)), Swiss-Prot Protein Knowledgebase (Swiss Institute of Bioinformatics), PROSITE Database of Protein Families and Domains, Database of Interacting Proteins (Univ. of California), Pfam Protein families database of alignments and HMMs (Sanger Institute), PRINTS (Manchester University), SUPERFAMILY Library of HMMs, neXtProt, InterPro, DisProt Database of experimental evidences of disorder in proteins (Indiana University School of Medicine, Temple University, University of Padua), MobiDB Database (University of Padua), Zebrafish Information Network, UCSC Malaria Genome Browser, RGD Rat Genome Database, The 1000 Genomes Project, BioCyc Database Collection including EcoCyc and MetaCyc, BRENDA (Comprehensive Enzyme Information System, including FRENDA, AMENDA, DRENDA, and KENDA), KEGG PATHWAY Database (Univ. of Kyoto), MANET database (University of Illinois), PubMed, FINDbase (the Frequency of INherited Disorders database), RIKEN integrated database of mammals, Barcode of Life Data Systems, Cellosaurus, (cell lines), CTD The Comparative Toxicogenomics Database (describes chemical-gene-disease interactions), DiProDB, Dryad (a repository of data underlying scientific publications in the basic and applied biosciences), Edinburgh Mouse Atlas, EPD Eukaryotic Promoter Database, MethBase Database on the UCSC Genome Browser, Minimotif Miner, Oncogenomic databases (compilation of databases that serve for cancer research), The Cancer Genome Atlas (TCGA), TDR Targets A, TRANSFAC, Reactome (Ontario Institute for Cancer Research, European Bioinformatics Institute, NYU Langone Medical Center, Cold Spring Harbor Laboratory), WikiPathways, BiGG Models, Personal Genome Project: RefSeq, SNP/Disease Databases, OMIM Online Mendelian Inheritance in Man, OMIM Inherited Diseases, HapMap, 23andme's database, Neuroscience Information Framework (University of California, San Diego), ConsensusPathDB, Entrez (National Center for Biotechnology Information) are some examples of highly organized data banks that may be queried in the practice of this invention.

An example listing of open format sources is maintained by HUGO Gene Nomenclature Committee (HGNC) which listed the following databases Jan. 20, 2018. As of January 2018, the HGNC list is continuously updated.

HUGO Gene Nomenclature Committee (www.genenames.org/useful/genome-databases-and-browsers).

Human Genome Databases, Browsers and Variation Resources

Database of Genomic Variants
dbVar Database of Genomic Structural Variation
ENCODE Project ENCyclopedia Of DNA Elements
Ensembl Human human genes generated automatically by the Ensembl gene builder
Entrez Gene searchable database of genes, defined by sequence and/or located in the NCBI Map Viewer
Genome Reference Consortium Putting sequences into a chromosome context
GWAS Central centralized compilation of summary level findings from genetic association studies
HapMap international HapMap Project
H-Invitational Database an integrated database of human genes and transcripts
Human Genome Segmental Duplication Database
Human Structural Variation Database
1000 Genomes A Deep Catalog of Human Genetic Variation
UCSC Human Genome Browser Gateway
VEGA Human manual annotation of finished genome sequence Other Vertebrate Genome Databases and Browsers AgBase a curated, open-source resource for functional analysis of agricultural plant and animal gene products
AnolisGenome a community resource site for *Anolis* genomics and genetic studies
ARKdb species databases includes: Cat, Chicken, Cow, Deer, Horse, Pig, Salmon, Sheep, Tilapia, Turkey
BirdBase A Database of Avian Genes and Genomes
Bovmap mapping the Bovine genome
Lyons Feline & Comparative Genetics
Chicken Genome Resources
The Dog Genome Project
Ensembl genome databases for vertebrates and other eukaryotic species
Entrez Gene searchable database of genes, from RefSeq genomes, defined by sequence and/or located in the NCBI Map Viewer
Fugu the Fugu genomics project
Horse Genome Project
Kangaroo Genome Project
lizardbase a centralized and consolidated informatics resource for lizard research
MGI Mouse Genome Informatics
National Animal Genome Research Program
Pig Genome Coordination Program
Porcine Genome Sequencing Project
Pig Genome Resources
Rabbit Genome Resources
RGD Rat Genome Database
*Tetraodon* Genome Browser
UCSC Genome Bioinformatics
VEGA Vertebrate Genome Annotation containing manual annotation of vertebrate finished genome sequence
Xenbase a *Xenopus* web resource
ZFIN Zebrafish Information Network Non-Vertebrate Genome Databases and Browsers ANISEED Ascidian Network for InSitu Expression and Embryological Data
AspGDAspergillus Genome Database
BeetleBase the model organism database for *Tribolium castaneum*
Cacao Genome Database
*Caenorhabditis* Genome Sequencing Projects
*Candida* Genome Database
ChlamydDB database for the green alga *Chlamydomonas reinhardtii* and related species
The Cotton Genome Database
*Daphnia* Genome Database Non-Vertebrate Genome Databases and Browsers
-continued Dendrome A Forest Tree Genome Database
dictyBase central resource for Dictyostelid genomics
EcoGene the Database of *Escherichia coli* Sequence and Function
Ensembl Genomes
FlyBase a database of the *Drosophila* genome
GenProtEC *E. Coli* genome and proteome database
GOBASE the Organelle Genome Database
Gramene a resource for comparative grass genomics
HGD Hymenoptera Genome Database
IGGI International *Glossina* Genome Initiative
PomBase a scientific resource for fission yeast
SGD *Saccharomyces* Genome Database
SpBase *Strongylocentrotus purpuratus* Sea Urchin Genome Database
StellaBase *Nematostella vectensis* Genomics Database
TAIR The *Arabidopsis* Information Resource
VectorBase invertebrate vectors of human pathogen
WormBase the biology and genome of *C. elegans*

As a metaphorical explanation to assist in understanding the methods of the present invention, a first ring of information surrounding the original SDI is collected. This ring comprises attributes, characteristics, hypotheses, symptoms, correlated symptoms or diseases, etc., relating directly to the SDI. Risk factors, trends in disease progression, commentaries by SDI afflicted individuals and friends and families may be included. A weighting system-algorithm or set of algorithms is preferentially used to rank elements of this ring. A set comprising each element or a set comprising predominant elements of this first ring is then subjected in a second cycle of analysis thereby producing a second ring.

This second ring will relate to the SDI through the first ring and thus share attributes, e.g., an affected gene, a misfolded protein, an enlarged mitochondrial pool, an out of range measurement, a shift in percentile rank, etc.—any remarkable (event deviating from normal or expected course) characteristic becomes an element of this second ring. Analysis of this second ring can broaden out to form third, fourth, fifth rings etc. These rings need not be exclusive. E.g., an element of said second ring may become an element of a third ring when indicated by one or more elements sharing the second ring. As analyses progress, a multi-dimensional picture will often result. Selective algorithms to gather associations and relationship information are preferentially applied at various stages in analysis to emphasize specific, high likelihood elements to guide progress.

For example, a symptom or disease in the second, third, etc., ring may have been the target—intended or accidental—during a successful, partially successful and or failed clinical trial. Sub-clinical experiments are not ignored, but in the following example clinical trial will be discussed to assist understanding of the process.

Data elements should not be prejudged. A failed clinical trial for example, may have been considered a failure relating to a different population, a different symptom or disease, a different criterion for success, a different standard for quality control, a loss of funding, etc., may have been a major contributing factor. Trial information may reside as elements in, e.g., a third ring. A failed compound may be repurposed, e.g., applied to a different disease element, administered by a different route, delivered to an identified set of patients—perhaps a subset of patients with specific criteria such as absence of a particular mutation to avoid risks, combined with a compound to block or mitigate undesired side effects, chemically stabilized, isomerically stabilized, etc. The highlighted compounds will be those previously shown or expected to have a high probability to interact with one or more of the disease symptoms. Testing may indicate one or more compounds may be better utilized, that is repurposed, for a disease or symptom at variance from the initiating search.

For example, analysis may determine that a potential pharmaceutical may have compromised effectiveness because inflammation interferes with its access to the target site. In another example, analysis may suggest a reason a potential pharmaceutical was less preferred or deselected was due to its association with inflammation. A combination pharmaceutical comprising the target active compound with one or more anti-inflammatory compounds might after expedited testing using features of the present invention produce a novel pharmaceutical composition with improved more acceptable efficacy. Another example might be a compound that was associated in some patients with oxidative damage. One or more antioxidants or stimulators of antioxidant activity (such as by the ubiquitous GSH) might then be formulated as a novel compound to effectively manage the targeted symptom or disease. Such anti-inflammatory compound(s) in the pharmaceutical composition, antioxidants and/or other components may be synthetic or may be derived from a natural, e.g., bacterial, fungal, plant or animal origination. Other coordinating drugs that may be useful in improving pharmaceutical compositions formulated in accordance with this invention include, but are not limited to: antiemetics, alpha and/or beta adrenergic active compounds, analgesics, muscle relaxers, stimulants, caffeine, etc. A composition may comprise one or more compounds with multiple ameliorative effects.

Repurposing may involve discarding a lead compound and elevating a candidate that in the original program was lower in the development hierarchy. Reasons may be varied and may have changed in the intervening time. For example, an earlier racemate may see a single optical enantiomer supplant it. As a historical example, modafinil is a racemic pharmaceutical with, when rapidly metabolized, potential liver toxicity restricting its maximal concentration. The L-enantiomer is metabolized more rapidly a) reducing its bioavailability and because of the rapid turnover risking hepatic damage; b) the R-enantiomer is metabolized more slowly so its biologic half-life is extended. The extended half-life is due to a reduced affinity for and/or reduced induction of CYP3A4/5. This reduced rate of metabolic decomposition reduces potential and observed toxicity. The armodafinil (R-enantiomer) thus is more effective when administered at the standard racemic dose due to its reduced metabolism and extended biological half-life and is less toxic for the same reason. Armodafinil is therefore prescribable at increased (and more effective) concentrations at a reduced risk to benefit ratio.

Another famous racemic distinction is that of thalidomide, where the desired pharmaceutical effects are obtained from the S-enantiomer. It is believed that the R-portion of the racemate is chiefly responsible for the drug's teratogenic effects. However, simply delivering the S-enantiomer to patients is not an option in this drug since the enantiomers auto-racemize. Stabilizing the chiral center of such drugs is one repurposing example.

In similar racemic situations the present invention can provide rapid suggestion of possible redirection of use for repurposing and may suggest congeners with minor chemical modification, e.g., stabilizing a chiral center, reducing or increasing lipid and/or aqueous solubility, etc. Additional data obtained subsequent to a failed trial (perhaps real or in silico crystallization with substrate) may suggest repurposing success probability would be increased by a slight change in the pharmaceutical geometry. Although not necessary for effectiveness of the invention the process may be embellished by analysis of possible congener compounds, for example as seen with hydrocodone and hydroxycodone. Such opportunities would be discoverable in accordance with this invention following the massive multi-dimensional processing of data. Accordingly, the present invention will not exclude optical isomers, structural isomers, morphologic isomers, congeners or close analogues of the active site(s) of the candidate pharmaceutical. Morphometric analogues are also viable candidates for such analysis. In many cases in silico analysis for criteria including, but not limited to: shape, solubility, active site stability, bioavailability, hepatic toxicity, thermal stability, biologic half-life, renal clearance, etc., will operate as a first stage or screen for selecting test candidates.

Another component of the present invention may make major use of genetic information. Crudely, phenotypic expressions have guided past practice for managing genetic diseases, such as sickle cell anemia, cystic fibrosis, etc. Complete or partial genomic sequence information can now guide repurposing processes by recognizing a genetic abnormality. Frequently a phenotypic expression may not present because a parallel or alternate pathway compensates for the dysfunctional gene. Using genomic information in combination with other features in the database system, i.e., multiple pathway information in this example, may serve to suggest repurpose of a failed candidate, for example, in an orphan drug environment, and/or may allow repurposing a generic drug to an orphan disease.

The genetic material in all its available tissue sources and formats allows for a primary or preliminary association with a disease and one or more of its expressed symptoms. In general human derived data will be most relevant, but comparisons with domains found in genomes of other organisms may sharpen decisions relating to alternate theories. Some human mutations may have no discernable effect, while data analysis may reveal unexpected correlations and possible or probable causations.

The symptoms, phenotypic expressions, resulting from different genomic functionalities, are considered for each disease while other occurrences of the symptom(s) or reversal of the symptoms are analyzed in a database structure, the structure of which preferably permits cross-association of a plurality of corresponding features including, but not limited to: symptom, disease, age, gender, blood type, HLA status, mass, girth, height, hair color, collection time, details of collection procedure and components used, comparison to a standard, source of sample, genomic information, epigenomic information, cDNA, mRNA, viral component, cell hydration, individual hydration status, source of hydration, expression profile, stimulus prior to or coincident with producing said feature(s), bioassay information, pharmaceuticals present or halted, physiologic data, biochemical data, nutrition status, ion balance (that may include one or more metallic ion, pH, polyatomic ions, counterions, charged biomolecules, amphipathic molecules, zwitterions, etc.) imaging information, activity(ies) related to feature development, etc. "Corresponding features" are features attributable to a database record where a plurality of features in said record are listed as being coincident in that record classification, for example: a person; a disease; characteristics of a symptom, disease, mutation; collection criteria, etc. (in essence any information associated with the source of the record or the record itself). Other diseases sharing one or more symptom are noted. Biomolecules, including, but not limited to: peptides, proteins, carbohydrates, glycoproteins, lipids, phospholipids, glycolipids, nucleoproteins, nucleic acids, vitamins, alcohols, precursors, metabolites, etc., are assimilated from these data analyses. Each available level of phenotypic expression is preferably analyzed to maximize analytical outcomes. The phenotypic expressions are most informative when analyzed across large populations and multiple diseases. Animal diseases, since they may derive from analogous genes or motifs, should not be eschewed in analysis. And since animal models are often useful and sometimes necessary for confidence in understanding a human disease, non-human genomic information should be considered relevant in many analyses.

The processes of the present invention using the "ringing" approach can be used to recognize related diseases where multi-expression outcomes might arise from a single defective gene.

For example a variety of auto-immune diseases including, but not limited to: diabetes, thyroid disease, multiple sclerosis, obesity, Addison's Disease, Severe Combined Immunodeficiency, asthma, some forms of Alzheimer's Disease, Lupus, etc., have been associated with variants of a C-type lectin domain family 16 member A (CLEC16A) gene. CLEC16A dysfunction is only a risk factor for several auto-immune diseases. Since the gene expression is one factor driving recycling of defective mitochondria, disease might be expected to be exacerbated when mitochondrial damage rises. Age, gender, nutrition, reactive oxygen stimulation, glutathione deficiency, etc. modulate risk. Correlations and/or other modulating influences can be identified in silico during practice of the invention.

The different undesired outcomes seen with respect to, for example, CLEC16A, arise from the dynamism of the cell and organism. No chemical reaction operates in isolation. For example, membrane potential acts as an electric field orienting charged particles such as proteins to a lower energy state, i.e., tending to neutralize the electric field. So the simple action of alignment—no covalent bonds formed or broken will affect alignment and position of other proteins. Alignment can be a critical feature, for example, forcing a receptor or enzyme active site to face a particular compartment in the organism or cell of the organism. Many different factors may influence alignment.

Another illustration is seen with chemicals that may be used in different reactions. First, the reaction can only occur when the two reactants are in contact and properly aligned. For example, adenosine triphosphate (ATP) is a high energy compound that supplies chemical energy to drive thousands of different biochemical reactions. By when an ATP is hydrolyzed to provide energy driving another reaction, that ATP molecule is consumed (split into phosphate and ADP) and thus every reaction that consumes an ATP reduces the proclivity for competing ATP consuming reactions. Similarly, cells have found many uses (different chemical pathways and outcomes) for the antioxidant, glutathione. Reduced glutathione is a tripeptide (GSH—glutamine, cysteine and glycine) electron donor. When GSH gives up an electron and is reversibly oxidized through formation of a disulfide bridge with another oxidized GSH to form GSSG while reducing other possibly damaging oxidizing (including several highly damaging reactive oxygen species (ROS)), potential downstream ROS damage from that active species molecule is eliminated and total oxidative toxicity reduced. GSH is used especially in hepatocytes to metabolize drugs and other foreign chemicals. But, when the GSH is oxidized to break down one drug molecule, that GSH cannot process the next molecule—and must be reduced before participating in the next reaction. The enzyme involved in metabolizing the drug molecule is also, while busy with the first, incapable of other reactions. Thus the longer the reaction takes, the greater the need for increased supply, e.g., induction, of the metabolizing enzyme such as a CYP.

In this respect, CLEC16A has multiple effects. CLEC variants have been associated with disparate diseases including, but not limited to: diabetes, adrenal dysfunction, reduced bone mineral density (BMD), Parkinson's disease, multiple sclerosis, etc. Differences in disease occurrences were observed to relate to gender, age, presence of variants of other genes, previous or current use (exposure) to pharmaceutical treatments, etc. Several symptoms of one or more of these diseases correlated with one or more symptoms of other diseases. A strong autoimmune component in the reduced BMD was not obvious. But a commonality observed in these disease states is lowered $O_2$ consumption and less ATP produced in affected cells. The $O_2$-ATP drop derives from inadequate mitochondrial metabolism.

The connection with CLEC16A was not directly apparent as pharmaceutical treatments for the disparate diseases were investigated. As this fortuitous exemplary compilation of research from multiple laboratories grew over decades of research, the relationships of the diseases to mitochondria and now to CLEC variants are becoming more apparent and are beginning to govern research strategies in the family of CLEC related diseases. The present invention, rather than relying on time and fortuitous relationships applies a process to identify potential relationships.

Genomic screening and correlation analyses associated CLEC16A with multiple and disparate autoimmune disorders leading many researchers to attempt to connect the gene, its expression patterns and products to autoimmune disease development. Review of the literature reveals that often only small numbers of proteins in the pathways connecting CLEC16A to mitochondria/$O_2$/ATP are investigated or discussed in the majority of papers. Patent application WO 2004108079 A2 discusses methods for developing drugs for possible use in treating Parkinson's disease as the interaction of Neuregulin receptor degradation protein-1 (Nrdp1) with the Parkin protein. Overexpression of Nrdp1 significantly reduced the endogenous Parkin level in an Nrdp1 dosage-dependent and proteasome-dependent manner. More importantly, Nrdp1 ubiquitinated Parkin and catalyzed the poly-ubiquitin chains on Parkin in vitro as well as in cells, indicating Parkin is an Nrdp1 substrate. In addition, we demonstrated that overexpression of Nrdp1 increased the production of reactive oxygen species (ROS), which was abrogated by co-expression of Parkin. Conversely, suppression of Nrdp1 by shRNA conferred SH-SY5Y cells a lower ROS level. Together, we provided evidence that interactions between Nrdp1 and Parkin negatively regulated Parkin level and affected ROS production, suggesting that Nrdp1 may play a role in Parkinson's disease.

A pseudo-random snippet of various papers and findings is discussed as illustrative of the arduous processes that can be involved in relating a root cause to a variety of downstream diseases. This brief selection leaves out the majority of published research in the fields but provides a glimpse of the complex integrations involved in following traditional patterns of research for drug discovery. It is understood that mitophagy is a cellular quality control pathway, which is essential to eliminate unhealthy mitochondria. See e.g., Diabetes 2017 November; db170321.

Furong Yu & Jianhua Zhou (Neuroscience letters. 440. 4-8. 10.1016/j.neulet.2008.) teach that Parkin is ubiquitinated by Nrdp1 and results in abrogation of Nrdp1-induced oxidative stress. They used interfering RNA molecules to confirm that reduced ROS was assocoated with Nrdp1 expression and that in other cells overexpression of Nrdp1 increased ROS.

Kageyama et al (The EMBO journal, 33(23), 2798-2813) report that: Parkin-independent mitophagy requires Drp1. Mitochondria enlarge and accumulate ubiquitinated outer membrane proteins and mitophagy adaptor protein p62 independently of Parkin. Drp1 deficiency causes mitochondrial dysfunction. And simultaneous loss of Drp1 and Parkin worsened cardiac defects.

DECIPHER (decipher.sanger.ac.uk/gene/CLEC16A#overview/clinical-info) confirms the RNF41/NRDP1-PARK2 pathway regulates autophagosome-lysosome fusion during late mitophagy. [RNF41 is the gene expressing Drp1.]

Durcan & Fon (Autophagy Vol. 11, Iss. 2, 2015) observe that the Parkinson disease (PD)-associated E3-ubiquitin (Ub) ligase PARK2/Parkin plays a central role in many stress response pathways, and in particular, in mitochondrial quality control. At least one form of Parkinson's disease is associated with thePARK2 gene, but other etiologies affecting PARK2 may be involved in interrupting the mitophagy pathway.

Larson-Casey et al (Immunity 44, 582-596, Mar. 15, 2016) teach that Akt1 induced macrophage mitochondrial reactive oxygen species (ROS) and mitophagy.

Tam et al (Exp Cell Res. 2017 Mar. 15; 352(2): 304-312) describe human CLEC16A regulation of autophagy by modulating mTOR activity. Overexpression of CLEC16A sensitizes cells towards the availability of nutrients with a heightened mTOR activity. This diminishes LC3 autophagic activity following nutrient deprivation. CLEC16A deficiency, on the other hand, delays mTOR activity in response to nutrient sensing, providing an augmented autophagic response. CLEC16A physically resides in cytosolic vesicles and the Golgi. Nutrient removal promotes clustering within the Golgi. They suggest that Golgi-associated CLEC16A negatively regulates autophagy via modulation of mTOR activity, and through this route may provide support for a functional link between CLEC16A and autoimmunity.

Swanberg et al (PLOS ONE, 2012) report that polymorphisms in the inflammatory genes CIITA, CLEC16A and IFNG influence BMD, bone loss and fracture in elderly women.

Soleimanpour et al (Cell Volume 157, Issue 7, 19 Jun. 2014, Pages 1577-1590) teach that type 1 diabetes susceptibility gene Clec16a interacts with E3 ubiquitin ligase Nrdp1. Clec16a via Nrdp1 regulates autophagosomal trafficking during late mitophagy. Clec16a regulates pancreatic β cell function through control of mitophagy. Clec16a controls β cell function and prevents diabetes by controlling mitophagy. And suggest that the CLEC16A/Nrdp1 pathway could be targeted for prevention and control of diabetes and may extend to the pathogenesis of other Clec16a- and Parkin-associated diseases.

In a subsequent report, Soleimanpour et al (Diabetes. 2015 October; 64(10):3475-84) relate type 2 diabetes to the mix with the following observations: Pdx1 regulates the expression of Clec16a, a type 1 diabetes gene and itself a key mediator of mitophagy through regulation of the E3 ubiquitin ligase Nrdp1. Restoration of Clec16a expression after Pdx1 loss of function restores mitochondrial trafficking during mitophagy and improves mitochondrial respiration and glucose-stimulated insulin release. Pdx1 orchestrates nuclear control of mitochondrial function in part by controlling mitophagy through Clec16A.

Pearson et al (Diabetes 2017 November; db170321) report Clec16A, Nrdp1, and USP8 form a Ubiquitin-Dependent tripartite complex that regulates beta cell mitophagy.

CLEC is a rare available example of looking through the pathways of seemingly unrelated diseases to begin to understand the commonalities and to suggest treatments closer to the root cause of the disease process. This involved decades of research in hundreds of laboratories and costs in the billions of dollars. The present invention still uses historical data developed around the world at great expense, but does not require sequential step-by-step understandings between hundreds of dispersed researchers to assimilate seemingly unrelated or possibly weakly related findings in a manner to more rapidly and economically associate diseases with other diseases sharing a root cause or related dysfunctional pathway.

Historical medicine including deaths, successful and failed treatments, evidence of selective pressures constitutes another valuable component of the optimized analytical framework. Treatments, including, but not limited to: conventional medicine, holistic, traditional, complementary, homeopathic, allopathic, etc., are assessed for relation to the original symptom(s) in question. Generally, these compounds will be known in the art and unpatentable as simple chemical material, but may be available, e.g., for repurposing in method patents, in combination with other compounds in compositions and/or in some cases as particular crystalline structures or at unexpectedly efficacious concentrations. Potential compositions and/or compounds are analyzed for their probable efficacy to the original symptom(s). Related symptoms are considered, for example, those relating to oxidative damage, ischemia, inflammation, etc., to propose optimal treatments for the original symptomatic disease as well as other diseases with one or more related symptom.

Previous experiences including traditional use, successful and unsuccessful medical trials, scientific literature, etc., are available for consideration. Many compounds will already have developed protocols for potential uses. Target biomolecules, cells, and then transgenic or knockout organisms can then be produced on a wide scale to assess the multiplicity of symptoms and related diseases to efficiently arrive at compositions for live animal and then human testing and marketing. Promising compounds and/or compositions are then delivered to a symptomatic individual or to a physical, chemical and/or bio model for assessing applicability to treating relevant symptoms in an individual. Compositions may be mixtures of a plurality of chemical compound entities in the same liquid, tablet, capsule caplet, solid matrix substance, etc., and may include mixtures occurring in the body and mixtures of one or more metabolites or reaction products of plural chemical entities delivered to a recipient in a single delivery event or a timed event. The composition as defined in this application may comprise none of the named chemical entities, instead comprising one or more metabolic products of same.

Biotechnology has advanced greatly to allow rapid production of transgenic and/or knockout cells and animals. Mice, being small inexpensively reproduced mammals are often a knockout organism of choice for screening. Genetic engineering has the capacity to "knockout" a gene or motif thereof to develop knockout cell lines or knock out animals. Transgenes—analogous genes taken from another species or modified with a preferred mutation—can now be inserted rather accurately to the targeted location. Using particular tools of such technology will depend on the nature of the target.

For greatest time efficiency the transgenic and/or knockout cells or organisms will be mass produced, i.e., in an assembly line type atmosphere to make hundreds or more different target organisms. For most rapid routes to the next stage in the production pipeline, the knockout or transgenic organisms do not require painstaking and time consuming validation. The validation stages can be deferred until promising data are obtained. This reduces the cost and time necessary for validating organisms that are not supportive of results.

While the pharmaceutical industry has successfully developed treatments for a multitude of human and animal diseases, many of the treatments are not ideal for reasons including, but not limited to: a) the treatments cause undesired effects (side effects), b) the treatments are merely treatments, not cures, c) the treatments have variable effectiveness across the population, d) the treatments have a limited period of effectiveness, etc.

Conventional procedures for developing a new drug comprise a lengthy and costly process. Estimates for bringing a new chemical entity (NCE) drug to market include a time frame of 10 to 15 years and a cost of $1 to $2 billion. NCEs may face limitations from patent and scientific literature disclosure describing the chemical entity which will not be considered "novel" even though a utility may not have been envisioned.

One response from industry has been a turn to biologic molecules, for example, antibodies as treatment compounds. The cost of development through human trials remains. But patent coverage as new compounds may be more readily available. However, competing antibodies against the same treatment target would also be considered novel allowing competitors to compete with or even replace the initial biologic.

In the absence of availability of strong patent protection, the importance of several years "data exclusivity" (a requirement that a new competitor drug go through the same trial process before coming on market as a competitor) provides a financial support for the massive costs for bringing new treatments to the marketplace.

An alternative approach has been a phenomenon dubbed "repurposing". Repurposing refers to a practice of finding alternative therapeutic indications for existing chemical entities including presently marketed rugs and drugs that may have failed efficacy tests in earlier trials. Ideally, a selected drug will have already been shown to be safe. This can significantly reduce the time and cost it takes to bring the drug to market. The earlier work regarding safety can make it more likely to get to market compared to an NCE. For a drug candidate with unsatisfactory efficacy in one proposed use the cost savings may be less, but still significant. If marketed as a supplement, the trial stage is not as rigorous, so costs are reduced. And even non-drugs, e.g., botanicals, may already be generally recognized as safe requiring no or just minimal safety confirmation of e.g., dosage. One famous repurposed drug is Viagra which failed on its testing for cardiovascular efficacy, but became a marketed blockbuster for its serendipitous effects on male erections that appeared as a side effect. Rogaine had a similar failure for its intended use, but was brought on the market to take advantage of a side effect instigating hair growth. Other such drugs suggesting effectiveness of repurposing include but are not limited to: Cymbalta, Gemzar, Evista, aspirin, ibuprofen, etc. Thus, this process has a proven utility and acceptability by regulators. At present in excess of 2000 previously approved pharmaceutical compounds have seen their initial NCE patent claims expire and are available for repurposing.

Despite possibly reduced costs, bring a new treatment to the public involves significant expenses at the start. If competitors were free to simply piggyback on the development and marketing of the new treatment, the absent financial incentive for improving medical treatments would rapidly bankrupt innovators and serve to disincentivize continued improvement in medicine. One incentive for repurposing can be found in "second medical use" patents that are available in many jurisdictions. In Europe two claim formats have been successful: The Swiss claim—"Use of substance X in the manufacture of a medicament for the treatment of condition Y" and the EPC2000 claim as a possible codified replacement or alternative—"Substance X for use in the treatment of condition Y". In the US various method claims are possible as well as Jepsom "the improvement being . . . " claims.

Irrespective of the format of the claim, a patent for a new medical use for a substance must be supported by evidence of efficacy. Several jurisdictions may require safety indications as support for utility.

Another potential pitfall in the patenting is lack of novelty due to inherency, especially when the treated symptoms and/or diseases are closely related. But attention in the description to differentiate related diseases and care in claim language can significantly reduce this risk.

Supplements have fewer restrictions on approval and marketing in the US. But the labelling may be an issue if referring to a specific health benefit. Accordingly, patenting is beneficial, especially when the beneficial outcomes are best achieved using a novel combination of materials, a pro-compound that is beneficially metabolized, and/or dose ranges that provide special benefit.

Another embodiment of the present invention features designing and producing novel chemical entities for treating a disease or class or group of diseases. This embodiment relies on similarities in a similar fashion as other embodiments, but instead of relying just on previously conceived compounds, applies database assessments to compile a plurality of compounds relating to a symptom, disease, symptoms relating to the original symptom or disease and disease featuring similar symptom(s). Chemical compounds with varying degrees of success in modulating one of more symptoms are assessed for similarities and distinctions. Structural features of promising compounds are incorporated into a chimeric compound or library of chimeric compounds, the chimeras maintaining the promising features while minimizing or eliminating features that according to database assessments were undesired for one or more reasons as determined form database analysis.

The present invention is not restricted to these compositions with available market exclusivity, though in many cases these advantages will induce producers to make and market products that improve healthy outcomes that benefit individuals and societies.

To answer the need for developing and marketing beneficial health supplements and/or novel treatments, the present invention provides a multi-step approach for discovering, screening, developing, optimizing and producing new treatments for symptomatic relief and treatment of disease (s).

A summarized example of this aspect of the present invention starts with a sub-optimal presentation of an individual. One or more deficiencies are catalogued, e.g., a sensory, defect, a motor defect, a cognitive defect, an adaptive defect, etc. In essence, any one or more biologic function(s) that is/are either hyper- or hypo-active may be addressed. Several approaches are available. For example, genomic information, including nuclear, mitochondrial, a specific tissue or organ, nucleic acid information, epigenetic information, etc., might be compared with corresponding information of other individuals either with or without aspects of the sub-optimal presentation. Symptoms obtained from a physical or mental assessment may be a part of the process. Bio-assays, including, but not limited to: blood, tears, sweat, mucus, semen, saliva, skin, tissue or organ biopsy, imaging, etc., may also be used. Assessments at sequential intervals or coinciding with one or more events or responses may be considered. Comparisons to one or more balancing states including, but not limited to: a "normal" or "more desired" status of the individual(s), a related individual, an individual presenting lesser of greater defect, a population, a sub-population (e.g., by genetic background, race, location, exposure, age, gender, size, mass, activity, physical characteristic, physiologic characteristic, previous pharmaceutical experience, profession, pain tolerance, etc.), a composite drawn from available data, etc., will often be an advantage in optimizing therapy.

Complaints/symptoms/observations associated with a disease state are catalogued and compared within a database collection for guidance from previous experiences. Specific biomolecules, often a protein, but not exclusively, may be associated with the individual's or individuals' symptom(s). One or more known chemical entity(ies) may already have a historical record in relation to the symptom(s) or biomolecule(s). The analysis need not be restricted to off-patent pharmaceuticals, withdrawn pharmaceuticals or failed pharmaceuticals, but might include any available evidence including, but not limited to: conventional medicine, holistic teachings, traditional concoctions, complementary therapies, herbal medicines, homeopathic therapeutics, allopathic composites, etc.

The data may be assessed using human or machine or a combination thereof. Artificial intelligence will become more efficacious with practice and experiences relating to successes and degrees of successes, which may include repurposing at any stage. For chemical entities, a NCE may be suggested by using the available data. For example, a slight change in permeability, electron donation or withdrawal capacity, partitioning between lipid and aqueous phase, reconfiguration of a binding site to increase or decrease affinity or reversibility of binding, reconfiguration of a binding site to alter geometry of the target, may be desired outcomes which may or may not require using a NCE. In rare instances it is possible that the data will overwhelmingly suggest a single compound or combination of compounds. However, in many instances alternatives will present each having its own special characteristics. With identified target molecules, in silico and in vitro assays may eliminate or elevate one or several alternatives as a screening pass. More elegant in vitro bioassays, in vivo cellular assays, in vitro synthetic tissue assays, ex vivo assays, in vivo cellular and/or animal assays may then be optimally applied for rapid and efficient confirmation and/or elimination of a compound or composition from consideration.

The application of database analysis at the early stage will have reduced time and cost. Similar or identical treatments for other diseases or disease states will expectedly be suggested. Accordingly, the development assays, with enlightened funding may branch to address other disease states. These branched programs may be accomplished by the instigating team or subbed out with involvement of other interested parties.

Rarely does a disease present with a single complaint or with identical symptoms in all affected patients. The complexity of the macro-organism's body requires multiple tissues and cell types, each with generally hundreds of anabolic and catabolic pathways and thousands of distinctive reactions that must be accomplished at appropriate timing. Accordingly, while a single protein may represent a major element in the disease initiation, maintenance and/or progression, other maladies accompany the major cause or the major contributor to the apparent symptom(s).

Many bacterial diseases have been successfully cured using anti-biotics. However, bacteria constantly evolve to develop resistance(s) to anti-biotic compounds thereby forming strains requiring novel therapies. Even when a bacterial disease is eliminated, on some occasions the immune response has produced cross-reactive antibodies that in addition to activating immune cell attacks on the bacterium also initiate immune attacks on the macro-organism's own tissue(s). Thus an auto-immune disease may linger following successful elimination of the pathogenic bacteria.

Viruses are micro-organisms known to cause many human diseases, such as measles, mumps, chicken pox, hepatitis, influenza, the common cold, etc. Viruses are considered obligate parasites because viruses require the host cell's energy and molecular machinery to produced descendants. To attain and maintain a cellular environment conducive for viral proliferation, the infecting viruses must strategically modulate host cells' metabolism and physiology to favor viral production. Viral infection thus often presents with a dramatic alteration of cellular and sub-cellular architecture and functions.

Mitochondria have become recognized as one of the key organelles in the maintenance of cellular homeostasis, metabolism, aging, innate immunity, apoptosis and other signaling pathways. At the intracellular level, the size, shape and motility of the mitochondria being under control of mitochondrial dynamics has become recognized as a key consideration for controlling many cellular processes. Mitochondria constitute a population of organelles that continuously fatten and/or elongate (by fusion), divide (by fission) and recycle their parts (by mitophagy). The processes of fusion, fission and mitophagy set a fundamental framework of mitochondrial dynamics. The mitochondrial dynamics (fusion and fission) in concert with mitophagy sustains mitochondrial homeostasis and constitutes an important arm of mitochondrial control of cell homeostasis.

The importance of mitochondria to a cell's healthy functions makes diverting these functions an important component for efficient and effective viral commandeering tof the cell to produce new viral entities. The role of mitochondrial dynamics in viral infections is scant and described only for few viruses. Mitochondria are often directly targeted by viral proteins or influenced by the physiological alterations to cellular environment during viral pathogenesis, e.g., deregulated calcium homeostasis, ER stress, oxidative stress and/or hypoxia.

Viruses interfere with the mitochondrial pathways and distort mitochondrial functions to facilitate viral proliferation. Viruses may affect mitochondrial activities including, but not limited to: fission, fusion, movement within the cell, movement between cells, $Ca^{++}$ concentrations and gradients, mitophagy, cell apoptosis, production of reactive oxygen species (ROS), control of innate immunity, etc. Mitochondria-mediated immune responses render them a target for invading pathogens including viruses. Viruses may either induce or inhibit mitochondrial processes in a highly specific manner to optimize production of viral progeny.

$Ca^{++}$ is an important factor for maintaining homeostasis and is recognized by viruses as an important target for controlling viral proliferation. For example:

The NS5A protein of Hepatitis C Virus (HCV) causes alterations in $Ca^{++}$ homeostasis, while the core protein of HCV targets mitochondria and increases $Ca^{++}$.

Protein X of hepatitis B virus (HBV) interacts with the mitochondrial outer membrane voltage-dependent anion channels (VDAC) to release of $Ca^{++}$ from storage organelles mitochondria, endoplasmic reticulum (ER), golgi into the cytoplasmic compartment to facilitate viral replication.

The Nef protein of HIV interacts with IP3R to induce an increase in cytosolic $Ca^{++}$ by promoting T cell receptor-independent activation of the NFAT pathway relating to intracellular $[Ca^{++}]$ oscillation, that assists the viral gene transcription and replication. $Ca^{++}$ is an important factor in different stages of rotavirus lifecycle and for stability to the virion through the NSP4 protein of rotavirus increasing cytosolic $Ca^{++}$ concentration. The pUL37x1 protein of human cytomegalovirus (HCMV) migrates to mitochondria to traffic of $Ca^{++}$ from the ER to mitochondria at 4-6 hrs post infection.

In addition to $Ca^{++}$ modulation, viruses control mitochondrial metabolism in other important manners:

Epstein-Barr virus (EBV) elicits increased oxidative stress in the host cells within 48 hrs.

This ROS event appears instrumental in virus release.

The mitochondrial antiviral signaling protein (MAVS) is cleaved by several viruses thereby reducing the cell's ability to produce anti-viral interferons.

Polio virus viroprotein 2B controls perinuclear redistribution of mitochondria and altered mitochondrial membrane permeability.

Pseudorabies virus and herpes simplex virus share an ability to inhibit mitochondrial transport through glycoprotein B and its effect on Miro and reduced recruiting of kinesin-1 to the mitochondria to facilitate their movement within the cell.

Protein PB1-F2 of influenza A indices mitochondrially-mediated cell-death.

Recognizing the multiple pathways involved in most diseases, including various cell organelles, especially mitochondria, is an important component in optimizing disease management, treatment or cure. This approach may often piggy-back on repurposing of pharmaceuticals, but, in several instances may merely serve to optimize existing therapy. For example, diseases affecting mitochondria will frequently include symptoms relating to $Ca^{++}$ metabolism, oxidative damage and/or cell death. Since mitochondria are primarily responsible for energetics of the mammalian cell, most diseases will have an overarching or underlying mitochondrial component.

The macro-organism comprises a multitude of cells to provide structure and function. Diseases in general affect cells, the active elements of the organism. The organism also is selfish in that it maintains its own self, but is unreceptive to foreign materials, such as pathogenic organisms that cause disease. The responsibility to eliminate the foreigner is the job of the immune system. When a cell becomes diseased it undergoes changes that often appear as foreign to the organism. As a result, a disease state often includes an inflammatory component. Reducing inflammation will not only reduce or eliminate one or often several disease symptoms, but will reduce swelling allowing better blood, lymph and interstitial fluid flow. The reduced tissue volume, especially in instances where extracellular blockades, such as plaque formations, may be present will physically disturb, i.e., serve to break up the intermolecular bonding of the plaque, and coincidently allow improved access of circulating fluids and cells for cleaning-up operations.

Inflammation and other disease sequellae often affect water and salt balance. Accordingly, optimal treatment for many diseases often will benefit from at least a period where salt balance hormones and/or drugs, including, but not limited to: arginine vasopressin (vasotocin), angiotensin II, natriuretic peptides, vasoactive intestinal peptide, urotensin II, insulin, corticosteroids, especially aldosterone, anti-diuretic hormone, renin, diuretic and anti-diuretic drugs are dispensed, released and/or controlled.

EXAMPLES

Example 1

Multiple individuals present with confusion. Following assessment symptoms correlate with those of a plaque deposition disease. A drug targeting plaque dimerization is discovered in one of the database depositions. Efficacy has been proven in vitro but of little long term benefit in vivo. Repurposing the drug compound as a composition pharmaceutical inclusive of an anti-inflammatory which reduces swelling and allows the repurposed drug to gain better access to its target not only slows disease progression but also shows slight regression.

Further in vitro analysis following in silico Monto Carlo like multi-drug analysis suggests that oxidation effects contribute to oligomerization of the protein forming the plaque. Several strong anti-oxidants are tested individually and in combination in silico and then for the most promising in silico combinations in vivo. Including an antioxidant capability in the composition shows further improvement in outcome associated with more rapid disappearance of the plaque protein complexes.

However, in several instances although plaque formations regressed, the patients show minimal improvement in mental clarity. Re-analysis using the database with an algorithm including an artificial intelligence component suggests that the anti-oxidation effect induces expression of another inflammatory interleukin. It is not determinative whether this results from attracting a different population or different maturity of immune system cells. The data simply show an associative (and suggestive) effect. The anti-oxidant in the composition is switched to an alternative that does not induce the suspect interleukin. Resulting treatment is further optimized using the improved composition.

Example 2

An individual presents with a sleep disorder including a form of apnea. Treating the sleep disorder using a generic drug is partially effective. However, apnea persists. Database analysis suggests using an alternative pharmaceutical that has been tested for hypertension due to its effect on water and salt balance. Anorexic insomnia was one of the side effects leading to its dismissal as a viable drug candidate for hypertension. This drug however is successfully repurposed for controlled and predictable sleep pattern with the added advantage of reducing obstructive apnea through improved water retention balance.

Although the individual demonstrates improved sleep habits, her energy levels are subnormal. Oxygen metabolism is also-subnormal. A composition combining the wakefulness balancing drug with a mitochondrial supporting cocktail restores activities to within those considered within a normal range.

Example 3

An individual presents with a cutaneous rash. Blood and skin bioassays suggest an autoimmune condition. Immune suppression involving prednisolone commences. Dosing is adjusted as the conditions shows improvement. But complete weaning is not successful. Further testing and algorithmic analysis using the database system shows an association with a mitochondrially induced hyper-oxidative state wherein oxidized protein components continue to stimulate the immune system rendering it hypersensitive to harmless metabolite components the body is in the process of eliminating. The algorithm followed by in silico testing suggests balancing glucose oxidation in mitochondria should reduce superoxide production which analysis suggests is the free-radical oxidative donor at the root of the problem. A composition pharmaceutical initially inclusive of the steroid anti-immune hormone is delivered to the individual. As successful treatment progresses a modified composition improved by reference to the database system using serial bioassays from the individual eliminates the steroid hormone but retains a combination of mitochondrial support drugs and supplements.

Component Examples

The following lists of compounds are provided as suggestive examples of the types of pharmaceutical and supporting compounds that might be revitalized in some instances and incorporated as especially beneficial supporting components in therapeutic compositions.

Anti-oxidant and/or compounds that help maintain native protein folding conformation and protein-protein interactions include but are not limited to: thiol donors including, but not limited to: L-cysteine and N-acetylcysteine and analogues and metabolic precursors thereof, glutathione (GSH), coenzyme Q10 (CoQ10), α-lipoic acid, generally weaker but effective anti-oxidants including, but not limited to: THC, phytochemicals such as resveratrol and flavonoids, milk thistle, *gingko, biloba*, gotu-kola, different forms of bioflavonoids, 1,2 dithiolane-3-pentanoic acid, lipoate (α-LA$^-$), dihydrolipoate (DLA$^-$), vitamin E, vitamin C, riboflavin (B$_2$), L-creatine, L-arginine, L-carnitine, cyclosporin A, manganese, magnesium, zinc, carnosine, folinic acid, dichloroacetate, succinate, etc.

Prostaglandins (PG) e.g., PGA, PGA$_2$, PGB, PGB$_2$, PGC, PGD, PGD$_2$, PGE, PGE$_1$, PGE$_2$, PGE$_3$, PGF$_\alpha$, PGF$_1\alpha$, PGF$_2\alpha$, PGF$_3\alpha$, PGG, PGH, PGH$_2$, PGI, PGJ, PGK, and related biomolecules, including, but not limited to: prostacyclins, thromboxanes, prostanoic acid, 2-arachidonoyl-glycerol (an endocannabinoid), etc., and their inhibitors may be especially useful in specific targeting of diseases, symptoms and/or co-existing disease states, especially when in conjunction with several specific inhibitors relating to PG synthesis or blocking in general or only in selectively specific tissues wherein a therapeutic compound may preferentially be effective in tissues to which it can gain access or in tissues which express the isoform of the enzyme that the COX or similar inhibitor targets.

Resveratrol is a potent antioxidant with apparent involvement in mitochondrial biogenesis. Resveratrol acts through AMPK and SIRT1 and is involved in PGC-1α. α-lipoic acid is associated with rejuvenation and replacement of damaged mitochondria. This renewal becomes more prevalent as mitochondria age. DCA stimulates oxidative phosphorylation by inhibiting pyruvate dehydrogenase kinase. Succinate is an intermediate in the tricarboxylic acid cycle (making ATP), and participates in inflammatory signaling. Succinate dehydrogenase participates in electron transport as part of mitochondrial "Complex II". Melatonin demonstrates cell protectant activity though slowing apoptosis as it controls activity of aged or oxidatively stressed mitochondria involvement in leading the cell down the apoptotic pathway. The anesthetic, cocaine, has been observed as modifying Complex I activity in mitochondria.

Increased glutathione is known to protect mitochondria and the cell against damaging effects of the oxidative moieties produced in mitochondria such as: superoxide anion radical $O_2^-$, hydrogen peroxide, $H_2O_2$, and the extremely reactive hydroxyl radical ˙HO. Increasing intracellular glutathione content is possible by several methods including, but not limited to: supplying precursors for glutathione synthesis, e.g., N-acetylcysteine; increasing CoA, for example, by supplying its precursor pantothenic acid; making curcumin (a spice) available to the cell; and the analgesic drug flupirtine. Since glutathione is seen to increase throughout the cell, the antioxidant protection is not limited to the mitochondria.

β-carotene, lycopene, lutein, astaxanthin and zeaxanthin are popular carotenoids. These biochemicals demonstrate antioxidation properties. These tend to be lipophilic and thus often are found partitioned in membranes.

Phytoantioxidants, especially cannabinoids which may demonstrate multiple effects, including, but not limited to: cannabigerolic acid (CBGA) (antibiotic); cannabigerolic acid monomethylether (CBGAM); cannabigerol (CBG) (antibiotic, antifungal, anti-inflammatory, analgesic); cannabigerol monomethylether (CBGM); cannabigerovarinic acid (CBGVA); cannabigerovarin (CBGV), cannabichromenic acid (CBCA); cannabichromene (CBC) (antibiotic, antifungal, anti-inflammatory, analgesic); cannabichromevarinic acid (CBCVA); cannabichromevarin (CBCV); cannabidiolic acid (CBDA) (antibiotic); cannabidiol (CBD) ((antioxidant, anxiolytic, antispasmodic, anti-inflammatory, analgesic); cannabidiol monomethylether (CBDM); cannabidiol C$_4$ (CBD-C4); cannabidivarinic acid (CBDVA); cannabidivarin (CBDV); cannabidiorcol (CBD-C1); Δ$^9$-tetrahydrocannabinolic acid A (THCA-A); Δ$^9$-tetrahydrocannabinolic acid B (THCA-B); 6a,10a-trans-6a,7,8,10a-tetrahydro-6,6,9-trimethyl-3-pentyl-6H-dibenzo[b,d]pyran-1-ol, (Δ$^9$-tetrahydrocannabinol, THC) (analgesic, antioxidant, antiemetic, anti-inflammation); Δ$^9$-tetrahydrocannabinolic acid-C4 (THCA-C4); Δ$^9$-tetrahydrocannabinol-C4 (THC-C4); Δ$^9$-tetrahydrocannabivarinic acid (THCVA); Δ$^9$-tetrahydrocannabivarinic (THCV); Δ$^7$-cis-isotetrahydrocannabivarin; Δ$^9$-tetrahydrocannabiorcolic acid (THCA-C1); tetrahydrocannabiorcol (THC-C1), Δ$^8$-tetrahydrocannabinolic acid (Δ$^8$-TCA); Δ$^8$-tetrahydrocannabinol (Δ$^8$-THC), cannabicyclol (CBL); cannabicyclolicacid (CBLA); cannabicyclovarin (CBLV), cannabiesoic acid A (CBEA-A); cannabiesoic acid B (CBEA-B); cannabieson (CBE), cannabinolic acid (CBNA); cannabinol (CBN); cannabinol methylether (CBNM); cannabinol-C4 (CBN-C4); cannabivarin (CBV); cannabinol-C2 (CBN-C2); cannabiorcol (CBN-C1); cannabinodiol (CBND); cannabinidivarin (CBDV), cannabitriol (CBT); 10-ethoxy-9-hydroxy-Δ-6a-tetrahydrocannabinol (10-EHDT); 8,9-dihydroxy-Δ-6a-tetrahydrocannabinol (8,9-DHDT); cannabitriolvarin (CBTV); ethoxy-cannabitriolvarin (CBTVE), dehydrocannabifuran (DCBF); cannabifuran (CBF); cannabichromanon (CBCN); cannabicitran (CBT); 10-oxo-Δ-6a-tetrahydrocannabinol (OTHC); $Δ^9$-cis-tetrahydrocannabinol (cis-THC); 3,4,5,6-tetrahydro-7-hydroxy-α-α-2-trimethyl-9-n-propyl-2,6-methano-2H-1-benzoxocin-5-methanol (2H-iso-HHCV); cannabiripsol (CBR); trihydroxy-$Δ^9$-tetrahydrocannabinol (triOH-THC) may be especially efficacious in compositions that benefit from anti-oxidative support.

Phytoantiinflammatory compounds are numerous and include but are not limited to: curcumin, colchicine, resveratrol, capsaicin, epigallocatechin-3-gallate, quercetin. Numerous small molecule and biomolecule anti-inflammatory compounds have been proposed for clinic with varying successes. See, e.g., An update on Anti-inflammatory Compounds: A Review. The contents of which are hereby incorporated by reference.

The invention claimed is:

1. A method of identifying a compound that modulates at least one of a group of diseases, said method comprising:
   a selecting a first symptom or first disease;
   b feeding said first symptom or first disease into a search field of a structured database;
   c querying said at least one structured database for content of one or a plurality of records referencing said first symptom;
   d selecting at least one record referencing said first symptom;
   e correlating said first symptom with at least one recorded feature of said at least one record;
   f querying at least one structured database for content of one or a plurality of records referencing said at least one recorded feature;
   g listing one or more compounds and/or compositions related to controlling or attempting to control at least one symptom noted as a recorded feature in said one or a plurality of records referencing said at least one recorded feature;
   h identifying in said listing, and delisting compounds and/or compositions, if any, known to have been applied to controlling said at least one symptom; and:
   i delivering to a physical, chemical and/or biomodel at least one said one or more compounds and/or compositions, said at least one said one or more compounds and/or compositions listed in g and remaining after h;
   j(a) determining effect of said one or more compounds and/or compositions;
   k(a) selecting one or more compounds and/or compositions determined to have desired effect; and
   l(a) identifying at least one of one or more compounds and/or compositions selected in k(a) as said new pharmaceutical composition; or:
   j(b) selecting at least one alternate compound or composition, at least one of said compounds and/or compositions delisted in h;
   k(b) optionally noting one or more undesired outcome(s), if any, resulting from said at least one alternate compound or composition being applied to controlling said at least one symptom;
   l(b) selecting for confirming at least a second compound or composition, said at least one second compound or composition selected to contribute modulation of an activity selected from the group consisting of: countering said one or more undesired outcome(s) (optionally, if any), anti-oxidation, anti-inflammation, diuresis, anti-diuresis, anti-depression, hypertension, hypotension, naturesis, anti-naturesis, kalesis, anti-kalesis, mitochondrial fission, mitochondrial fusion, mitochondrial motility, ROS damage, $O_2$ consumption and interferon production;
   m confirming desired activity of said at least one second compound or composition; and
   n identifying as said new pharmaceutical composition, a composition comprising at least one said alternate compound to be used in conjunction with at least one said second compound said one or more compounds and/or compositions.

2. The method of claim 1 further comprising:
   delivering said new pharmaceutical composition to at least one individual.

3. The method of claim 2 wherein said delivering comprises providing an individual with a substance selected from the group consisting of: pill, tablet, osmotic pump, ointment, inhalant, eye drop, sublingual substance, mouthwash, pastille, gel, hydrogel, injection, subdermal implant, powder, emulsion, elixir, gum, cream, paste, liniment, liposome, skin patch, suppository, IUD, microsphere, nanosphere and nasal spray.

4. The method of claim 1 wherein said new pharmaceutical composition is applied to treating a second symptom or second disease wherein said symptom is not identical to said second symptom or said disease is not identical to said second disease.

5. A method for identifying a new pharmaceutical composition for treating a disease, said method comprising:
   a selecting a first symptom of a first disease;
   b providing an identification of said first disease;
   c accessing at least one structured database;
   d querying said at least one structured database for content of one or a plurality of records referencing said first symptom;
   e selecting at least one record referencing said first symptom;
   f correlating said first symptom with at least one recorded feature of said at least one record;
   g querying at least one structured database for content of one or a plurality of records referencing said at least one recorded feature;
   h listing one or more compounds and/or compositions related to controlling or attempting to control at least one symptom noted as a recorded feature in said one or a plurality of records referencing said at least one recorded feature;
   i identifying in said listing, and delisting compounds and/or compositions, if any, known to have been applied to controlling said at least one symptom; and:
   ja delivering to a physical, chemical and/or bio model at least one said one or more compounds and/or compositions, said at least one said one or more compounds and/or compositions listed in h and remaining after i;
   ka determining effect of said one or more compounds and/or compositions;
   la selecting one or more compounds and/or compositions determined to have desired effect; and
   ma identifying at least one of one or more compounds and/or compositions selected in l as said new pharmaceutical composition; or:
   jb selecting at least one alternate compound or composition, at least one of said compounds and/or compositions delisted in i;

kb optionally noting one or more undesired outcome(s), if any, resulting from said at least one alternate compound or composition being applied to controlling said at least one symptom;

lb selecting at least a second compound or composition, said at least one second compound or composition selected to contribute modulation of an activity selected from the group consisting of: a compound countering said one or more undesired outcome(s) (optionally, if any), anti-oxidation, anti-inflammation, diuresis, anti-diuresis, anti-depression, hypertension, hypotension, naturesis, anti-naturesis, kalesis, anti-kalesis, mitochondrial fission, mitochondrial fusion, mitochondrial motility, ROS damage, $O_2$ consumption and interferon production;

mb confirming desired activity of said at least one second compound or composition; and n as said new pharmaceutical composition, a composition comprising at least one said alternate compound to be used in conjunction with at least one said second compound said one or more compounds and/or compositions.

6. The method of claim 5 further comprising:
delivering said new pharmaceutical composition to at least one individual.

7. The method of claim 6 wherein said delivering comprises providing an individual with a substance selected from the group consisting of: pill, tablet, osmotic pump, ointment, inhalant, eye drop, sublingual substance, mouthwash, pastille, gel, hydrogel, injection, subdermal implant, powder, emulsion, elixir, gum, cream, paste, liniment, liposome, skin patch, suppository, IUD, microsphere, nanosphere and nasal spray.

8. The method of claim 5 wherein said new pharmaceutical composition is applied to treating a second disease wherein said first disease is not identical to said second disease.

9. A method for producing a new pharmaceutical composition, said method comprising:
a selecting a first symptom of a first disease;
b providing an identification of said first disease;
c accessing at least one structured database;
d querying said at least one structured database for content of one or a plurality of records selected from the group consisting of: record(s) referencing said first symptom and record(s) referencing said first disease;
e selecting at least one first record obtained from d;
f selecting at least one chemical compound relating to said at least one first record;
g querying at least one structured database for content of one or a plurality of records referencing said at least one chemical compound to obtain a listing comprising diseases and symptoms relating to said compound;
h querying at least one structured database with results of said listing obtained from the querying to obtain a compilation of compounds associated with symptoms or diseases of said listing;
i analyzing compounds related in f and h for similarities and distinctions;
j querying at least one structured database for negative assessments of compounds related in f and h;
k correlating negative assessments with similarities and distinctions of i;
l associating chemical structure with said similarities and distinctions;
m selecting chemical structural features minimizing said negative assessments;
n designing a chimeric compound or a library of chimeric compounds maintaining at least one feature of at least one compound related in f and h while discarding one or more chemical feature selected in m; and
o producing at least one compound designed in n.

10. The method of claim 9 further comprising:
e1 querying at least one structured database for a compound previously applied to modulate at least one characteristic associated with said first symptom or said first disease to obtain a compound identifying record; and
in f selecting a chemical compound relating to said compound identifying record.

11. The method of claim 9 wherein said new pharmaceutical composition is applied to treating a second symptom or second disease wherein said first symptom is not identical to said second symptom or said first disease is not identical to said second disease.

* * * * *